United States Patent
Wenstrom, Jr. et al.

[11] Patent Number: 5,984,927
[45] Date of Patent: Nov. 16, 1999

[54] DEVICE FOR SUTURELESS ATTACHMENT OF SOFT TISSUE TO BONE

[75] Inventors: Richard F. Wenstrom, Jr., Norwood; Gregory R. Whittaker, Stoneham, both of Mass.

[73] Assignee: Ethicon, Inc., Somerville, N.J.

[21] Appl. No.: 09/033,805

[22] Filed: Mar. 3, 1998

[51] Int. Cl.[6] .................................................. A61B 17/56
[52] U.S. Cl. .......................... 606/72; 606/73; 606/213; 606/75; 606/78
[58] Field of Search ............................... 606/72, 73, 213, 606/75, 78

[56] References Cited

U.S. PATENT DOCUMENTS

| | | | |
|---|---|---|---|
| 3,579,831 | 5/1971 | Stevens et al. | 606/73 |
| 4,976,715 | 12/1990 | Bays et al. | 606/77 |
| 5,129,906 | 7/1992 | Ross et al. | 606/77 |
| 5,261,914 | 11/1993 | Warren | 606/73 |
| 5,380,334 | 1/1995 | Torrie et al. | 606/104 |
| 5,417,712 | 5/1995 | Whittaker et al. | 606/232 |
| 5,478,342 | 12/1995 | Kohrs | 606/73 |
| 5,601,558 | 2/1997 | Torrie et al. | 606/72 |
| 5,800,436 | 9/1998 | Lerch | 606/72 |
| 5,840,078 | 11/1998 | Yerys | 606/73 |
| 5,849,004 | 12/1998 | Bramlet | 606/72 |

OTHER PUBLICATIONS

"Arthroscopic Shoulder Stabilization Using the Bioabsorbable Tack", Claude T. Moorman III, et al., Current Techniques in Arthroscopy, Chapter 13, pp. 125–132, not dated.

*Primary Examiner*—Michael Buiz
*Assistant Examiner*—Daphna Shai
*Attorney, Agent, or Firm*—Nutter, McClennen & Fish, LLP

[57] ABSTRACT

A device for sutureless attachment of soft tissue to bone has an elongate substantially cylindrical stud and a head disposed on a proximal end of the stud. The stud has a sidewall that defines a nominal diameter and the head has a diameter that is greater than the nominal diameter. At least one barb is provided to retain the stud within bone. The at least one barb may be constructed from a shape memory alloy and the stud and head may be constructed from a bioabsorbable material.

20 Claims, 2 Drawing Sheets

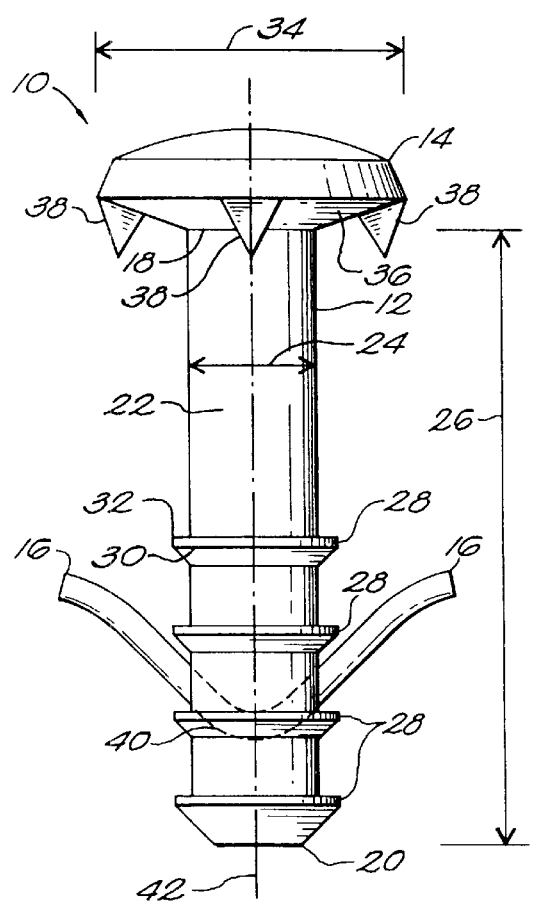
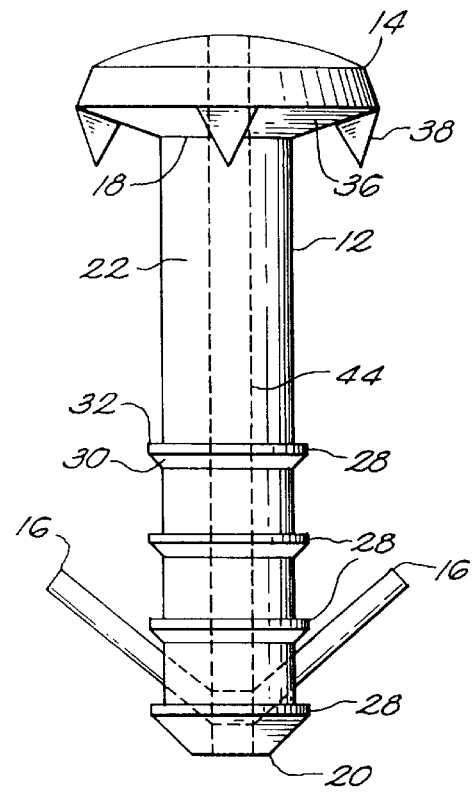
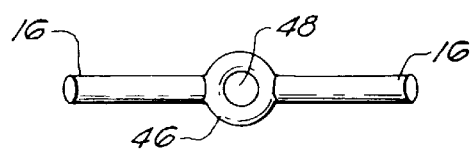
FIG. 1
FIG. 2
FIG. 3

DEVICE FOR SUTURELESS ATTACHMENT OF SOFT TISSUE TO BONE

FIELD OF THE INVENTION

The invention relates to tissue fastening devices. More particularly, the invention relates to a sutureless fixation device for attaching soft tissue to bone.

BACKGROUND OF THE INVENTION

Repair of torn soft tissue has changed dramatically over recent years. Generally, techniques for repairing soft tissue tears involve reattaching the torn tissue back to the bone from which it is avulsed. Typically, suture material is used to tie the tissue directly back to bone to facilitate healing of the tissue. Open techniques for reattaching soft tissue to bone often require large incisions, resulting in long periods of immobilization and rehabilitation for the affected tissues as well as increased morbidity resulting from the lengthy surgery.

More recently, closed techniques, and fixation devices for use in closed techniques, have been developed to relieve some of the disadvantages resulting from the use of open techniques to attach soft tissues to bone. Suture anchors are one type of device known for use in attaching soft tissue to bone in closed surgical procedures. Examples of such anchors and their use may be found in U.S. Pat. Nos. 4,898,156; 4,899,743; 5,207,679; 5,217,486; 5,417,713; and 5,522,845. Generally, a suture anchor is inserted into a preformed bore in a bone where the suture anchor fixes to an internal portion of the bone. A length of suture thread, either pre-threaded in the anchor or threaded through an eyelet in the anchor after insertion, is used to tie the injured tissue into place so that healing may occur.

In some instances, it may be preferable to attach the soft tissue to bone without the need to tie the soft tissue with suture thread. One type of device that has been developed to meet this need is the tissue tack. Tissue tacks, such as those shown in U.S. Pat. Nos. 4,976,715; 5,261,914; 5,380,334; and 5,601,558, generally have an elongate portion and a head portion. The elongate portion is passed through a hole in the tissue and into a preformed bore in a bone. The head portion has a larger diameter than the hole in the tissue and thus serves to secure the tissue to the bone when the elongate portion is inserted into the bore. Often, tissue tack devices are constructed from bioabsorbable materials so that further surgery is not needed to remove the tack when tissue mending is complete.

Generally, bone fixation elements on tissue tacks such as those disclosed in the U.S. patents listed above are limited to circumferential ridges disposed on the elongate portion of the tack which form a friction fit within the bore in the bone. While this form of bone fixation may be sufficient for patients with very high quality bone, it is insufficient for many other patients, especially older patients, who may have poor quality bone, osteopenic bone or bone that has been weakened by disuse due to pain. Accordingly, there remains a need for tissue tacks having improved bone fixation elements so that such tacks may be used with a wider variety of patients who could benefit from the use of tissue tacks.

SUMMARY OF THE INVENTION

The present invention provides a bio implantable device for sutureless attachment of soft tissue to bone. The device of the invention includes an elongate substantially cylindrical stud having proximal and distal ends and a sidewall defining a nominal diameter disposed between the proximal and distal ends. A head is disposed on the proximal end of the stud and has a diameter greater than the nominal diameter of the stud. The head also has a distal, tissue contacting surface. At least one barb extends outward and proximally from the sidewall of the stud and is effective to retain the stud within a bore in a bone.

In one embodiment, the head and stud are formed from an absorbable or nonabsorbable polymeric material and the barbs are elongate and formed from a shape memory material. The barbs may be connected to a central body which structurally connects the barbs to each other and to the stud. The central body may be an elongate, metal body having a distal, bone penetrating apex.

A longitudinal bore, useful for installing the device within bone, may be provided through the head and stud. A through hole may also be provided in the central body in communication with the longitudinal bore.

BRIEF DESCRIPTION OF THE DRAWINGS

The invention will be more fully understood by reference to the following detailed description when considered in conjunction with the accompanying drawings, in which:

FIG. 1 is an elevated view of a device for attaching soft tissue to bone of the invention;

FIG. 2 is an elevated view of an alternative device for attaching soft tissue to bone of the invention;

FIG. 3 is a superior view of a bone attachment element of FIG. 2; and

DETAILED DESCRIPTION OF THE INVENTION

Figure 4:
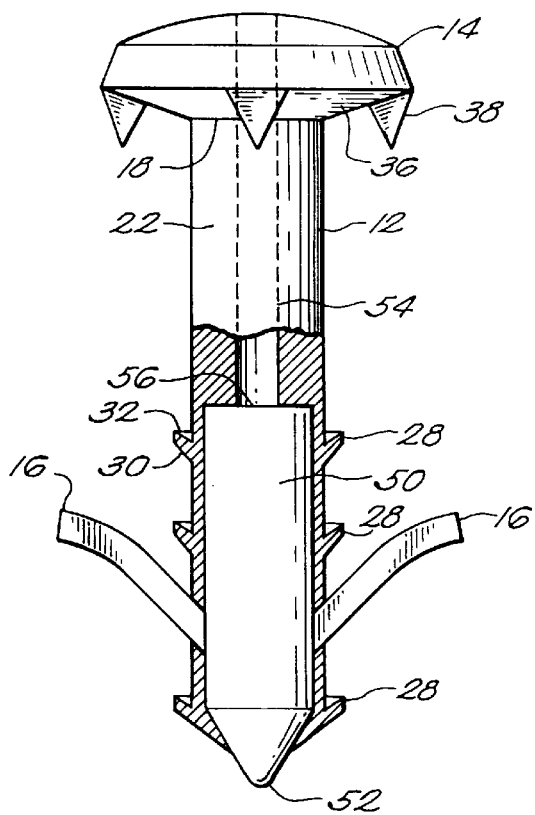
FIG. 4 is a view, partially in section, of another alternative device of the invention for attaching soft tissue to bone.

A bio implantable device 10 for attaching soft tissue to bone of the invention is illustrated in FIG. 1. This exemplary device includes an elongate substantially cylindrical stud 12, a head 14, and at least one barb 16. The stud 12 has proximal and distal ends 18, 20, and a sidewall 22 defining a nominal diameter 24 disposed between the proximal and distal ends 18, 20. While the dimensions of the stud 12 may vary depending on its intended application, generally, the nominal diameter 24 will be between about 2.7 and 4.2 millimeters and the stud 12 will have a length 26 between about 12.0 and 20.0.

One or more circumferential ribs 28 may be provided on the stud 12 extending outwardly from the sidewall 22 and beyond the nominal diameter 24. A person of ordinary skill in the art will understand that the circumferential ribs 28 may be constructed so as to aid in retaining stud 12 within a bore in a bone by forming a friction fit inside the bore. For example, the circumferential ribs 28 each have an angled distal face 30 which allows ease of insertion of the stud into a bore in a bone, but a sharp upper edge 32 (shown in cross section in FIG. 4) that engages bone tissue within the bore to resist withdrawal.

The head 14 is disposed on the proximal end 18 of the stud 12 and has a head diameter 34 that is greater than the nominal diameter 24 of the stud 12. In a typical embodiment, the head diameter 34 will be in the range of about 7.4 to 9.0 millimeters. The head also has a distal-facing surface 36. One or more tissue penetrating spikes 38 may be provided on the distal-facing surface 36. When the distal-facing surface 36 of the head 14 rests flush on the tissue being attached to bone, spikes 38 engage the tissue to hold it firmly in place.

In one embodiment, head 14 and stud 12 may be constructed of a polymer, such as ultra high molecular weight polyethylene (UHWPE), polysulfone, PEEK, Nylon or Delrin. Alternatively, head 14 and stud 12 may be formed out of any of the many bioabsorbable materials known in the art. Examples of such bioabsorbable materials include homo and copolymers of glycolide and trimethylene carbonate, homo and copolymers of lactide and glycolide, homo and copolymers of polylactic acid, or a blend of these homopolymers and copolymers. When formed from bioabsorbable materials, head 14 and stud 12 might also be coated with longer lasting materials such as caprolactone and glycolide homo and copolymers, or glycolide and lactide homo and copolymers. The exact composition of such head 14 and stud 12 elements will vary according to the absorption and rigidity characteristics desired.

At least one bone engaging barb 16 extends from the sidewall 22 of the stud 12. As shown in FIG. 1, two bone engaging barbs 16 extend outwardly and proximally from the sidewall 22. More or fewer bone engaging barbs 16 may be employed as required to ensure proper fixation of the device 10 in a bone. In this embodiment, a central body 40 structurally connects barbs 16 to each other and to the stud 12. Barbs 16 are typically disposed about a longitudinal axis 42 and cantilevered to the central body 40. Generally, barbs 16 are elongate and extend proximally from the stud at an angle between about 10° and 90° with the longitudinal axis 42. The length of barbs 16 should be sufficient to retain device 10 within a bore in a bone and the barbs 16 will generally extend outward between about 3.0 and 7.0 millimeters from the sidewall 22 of the stud.

In the embodiment shown in FIG. 1, central body 40 is formed integrally with and of the same material as barbs 16. However, the central body 40 may also be a separate structure made of a different material. Preferably, barbs 16 are formed out of a pseudoelastic shape memory alloy of the type disclosed in U.S. Pat. No. 4,665,906. By way of example, one such pseudoelastic shape memory alloy is a nickel titanium alloy such a Nitinol, which is available from Flexmedics of Minneapolis, Minn., among others.

The use of shape memory materials for barbs 16 permits the barbs 16 to initially deflect inward to the extent required to permit the anchor to be inserted into a bore in a bone, yet still resiliently "spring back" toward their normal, outwardly projecting position so as to prevent the device 10 from withdrawing back out of the bone hole or tunnel. Sidewall 22 may also be provided with grooves (not shown) aligned with barbs 16 so that when the barbs 16 deflect inward, they deflect into the grooves, allowing easier entry into the bone. In addition, barbs 16 so formed may be deflected inward before inserting the stud 12 through the tissue to be attached to bone, thus avoiding damage to the tissue by passing the extended barbs 16 there through.

The bio implantable device 10 of the invention may also include a longitudinal bore 44 through the head 14 and stud 12, as shown in FIGS. 2 and 3. Barbs 16 in this embodiment are attached to a circular central body 46 having a through hole 48 aligned with longitudinal bore 44. Provision of such a bore 44 and through hole 48 allow the bio implantable device 10 to be inserted into a bore in a bone by means of a K-wire or other guide means known in the art. For example, with a K-wire locked into and extending beyond a cannulated drill, the soft tissue to be attached can be penetrated and moved into position over the bone. The drill may then be used to form a bore of predetermined size in the bone. Then, the drill may be removed while leaving the K-wire in place in the bore so that the free end may be inserted into and through the longitudinal bore 44 and through hole 48 within the implantable device 10. The device 10 can then be guided along the K-wire, through the soft tissue, and into the bore in the bone.

Figure 5:
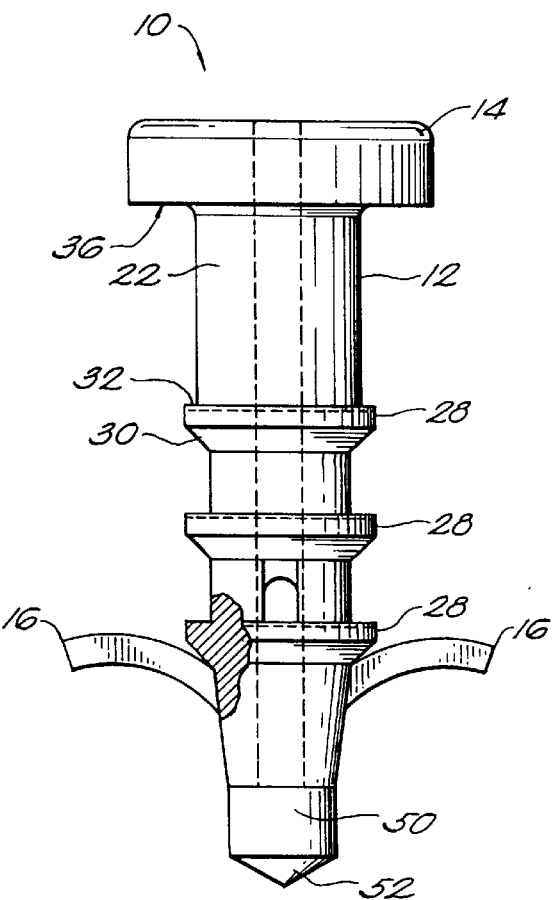
FIG. 5 is a view, partially in section, of an additional device of the invention for attaching soft tissue to bone.

The embodiments of the bio implantable device 10 of the invention shown in FIGS. 4 and 5 include a central body 50 formed in the shape of a conventional suture anchor. Central body 50 is elongate and substantially cylindrical with a distal, bone penetrating apex 52. As shown, the bone penetrating apex 52 extends beyond the distal end 20 of the stud 12 and may be used to locate the device 10 with respect to a preformed bore in a bone.

Central body 50 may be formed from any biocompatible material. In one embodiment, wherein the stud 12 and head 14 are formed from a bioabsorbable polymer and the device 10 and preformed bore in a bore are configured so that the central body 50 is positioned below the surface of the bone when the device 10 is deployed, the central body 50 is preferably formed from a metal such as titanium or a titanium alloy. In such an embodiment, after the bioabsorbable head 14 and stud 12 have been absorbed, the metal central body 50 and shape memory material barbs 16 need not be surgically removed from the patient because they are located beneath the surface of the bone. In addition, forming central body 50 of metal provides excellent support for the attachment of one or more barbs 16.

Device 10 may be provided with a blind longitudinal bore 54 (FIG. 4). This bore 54 extends from the head 14 to a proximal end 56 of central body 50. With such a bore 54, device 10 may be inserted using an appropriate tool (not shown) having an insertion pin that extends into the longitudinal bore 56 and abuts the proximal end 56 of central body 50. Such a tool may be used to drive device 10 into a preformed bore in a bone.

Although the present invention is described with respect to particular embodiments and features and uses, numerous variations or equivalents are possible without taking away from the spirit or scope of the claimed invention. All references cited herein are expressly incorporated by reference in their entirety.

What is claimed is:

1. A bio implantable device for attaching soft tissue to bone, comprising:

an elongate, substantially cylindrical stud having proximal and distal ends, and a sidewall defining a nominal diameter disposed between the proximal and distal ends;

a head disposed on the proximal end of the stud, the head having a diameter greater than the nominal diameter of the stud and having a distal-facing surface; and at least one bone penetrating barb extending outward beyond the diameter of the head and proximally from the sidewall of the stud, the at least one bone penetrating barb being unitary with the stud and being effective to retain the stud within bone.

2. The device of claim 1, wherein the at least one barb is constructed from a metal.

3. The device of claim 1, wherein the at least one barb is a deformable element constructed from a shape memory alloy.

4. The device of claim 3, wherein the at least one barb is elongate and extends proximally at an angle that is between about 10° and 90° with a longitudinal axis of the stud portion.

5. The device of claim 3, wherein the distal end of the stud further comprises a distal, bone-penetrating apex.

6. The device of claim 5, wherein the distal, bone-penetrating apex is formed on a distal end of a substantially cylindrical metal body, the at least one barb element being fixed to the metal body.

7. The device of claim 6, further comprising a longitudinal bore extending from the head to the metal body.

8. The device of claim 1, wherein the stud and the head are constructed from a bioabsorbable material.

9. The device of claim 7, wherein the stud and the head are constructed of a bioabsorbable material selected from the group consisting of homo and copolymers of glycolide and trimethylene carbonate, homo and copolymers of lactide and glycolide, homo and copolymers of polylactic acid, or a blend of these homopolymers and copolymers.

10. The device of claim 1, wherein the stud further comprises at least one circumferential rib disposed on the sidewall of the stud.

11. The device of claim 1, further comprising at least one tissue penetrating spike disposed on the distal facing surface of the head.

12. The device of claim 1, further comprising a longitudinal bore extending from the head to the distal end of the stud.

13. The device of claim 12, wherein the at least one barb is fixed to a central body having an aperture in communication with the longitudinal bore.

14. A bio implantable device for sutureless attachment of soft tissue to bone, comprising:

an elongate, substantially cylindrical stud constructed from a polymeric material and having proximal and distal ends, and a sidewall disposed between the proximal and distal ends that defines a nominal diameter, the stud including at least one circumferential rib disposed on the sidewall and having a diameter heater than the diameter of the stud;

a head integral with the proximal end of the stud portion, the head being constructed from a polymeric material and having a second diameter greater than the nominal diameter; and bone penetrating barb means extending from the stud outward beyond the diameter of the at least one circumferential rib for retaining the device within bone, the bone penetrate barb means being unitary with the stud.

15. The device of claim 14, wherein the barb means comprises at least one deformable barb element extending proximally from the stud at an angle between about 10° and 90° with a longitudinal axis of the device.

16. The device of claim 14, wherein the barb means comprises two deformable barbs constructed from a shape memory material and fixed to a central body.

17. The device of claim 16, wherein the device includes a longitudinal bore formed from the head to the distal end of the stud and central body includes an aperture in communication with the longitudinal bore.

18. The device of claim 16, wherein the central body comprises a metal, cylindrical body having a bone penetrating distal apex.

19. The device of claim 18, wherein the device includes a longitudinal bore formed from the head to the central body.

20. The device of claim 16, further comprising at least one circumferential rib formed on the sidewall of the stud, the at least one circumferential rib extending beyond the nominal diameter of the stud.

* * * * *

UNITED STATES PATENT AND TRADEMARK OFFICE
CERTIFICATE OF CORRECTION

PATENT NO. : 5,984,927
DATED : November 16, 1999
INVENTOR(S) : Richard F. Wenstrom, Jr.; Gregory R. Whittaker It is certified that error appears in the above-identified patent and that said Letters Patent is hereby corrected as shown below:

Column 5, Line 11      claim "7" should be claim "8"

Column 6, Line 2       "heater" should be "greater"

Column 6, Line 11      "penetrate" should be "penetrating"

Signed and Sealed this

Fifteenth Day of May, 2001

Attest:

NICHOLAS P. GODICI

*Attesting Officer*    *Acting Director of the United States Patent and Trademark Office*